(12) United States Patent
Konakawa et al.

(10) Patent No.: US 6,476,389 B1
(45) Date of Patent: Nov. 5, 2002

(54) X-RAY ANALYZER HAVING AN ABSORPTION CURRENT CALCULATING SECTION

(75) Inventors: Hiroshi Konakawa, Omiya (JP); Yasuhiko Sato, Omiya (JP); Seiichi Suzuki, Machida (JP)

(73) Assignees: Fuji Photo Optical Co., Ltd., Saitama (JP); Quark Inc., Tokyo (JP)

( * ) Notice: Subject to any disclaimer, the term of this patent is extended or adjusted under 35 U.S.C. 154(b) by 0 days.

(21) Appl. No.: 09/523,305

(22) Filed: Mar. 10, 2000

(30) Foreign Application Priority Data

Mar. 25, 1999 (JP) ............................. 11-080822

(51) Int. Cl.⁷ ............................. G21K 7/00; G01N 23/00
(52) U.S. Cl. ........................ 250/310; 250/306; 250/307
(58) Field of Search ................................ 250/307, 310, 250/492.2, 306, 252.1

(56) References Cited

U.S. PATENT DOCUMENTS

| | | | |
|---|---|---|---|
| 3,786,305 A | | 1/1974 | Komoda et al. |
| 5,128,545 A | * | 7/1992 | Komi ........................ 250/310 |
| 5,659,174 A | * | 8/1997 | Kaneoka et al. ............. 250/310 |
| 6,072,178 A | * | 6/2000 | Mizuno ....................... 250/310 |

FOREIGN PATENT DOCUMENTS

| | | |
|---|---|---|
| EP | 452 825 A2 | 10/1991 |
| GB | 2 255 253 A | 10/1992 |
| JP | 52-127292 | 10/1977 |
| JP | 63-086233 | 4/1988 |
| JP | 8-043331 | 2/1996 |

OTHER PUBLICATIONS

Japanese Patent Office, *Patent Abstracts of Japan*, Publication No. 63086233A, Date of Publication: Apr. 16, 1988, Application No., 61230776, Date of Filing: Sep. 29, 1986 English Language Abstract, Japanese Application pp 151–154.

* cited by examiner

*Primary Examiner*—John R. Lee
*Assistant Examiner*—David A. Vanore
(74) *Attorney, Agent, or Firm*—Snider & Associates; Ronald R. Snider

(57) ABSTRACT

In quantitative analysis of an element in a specimen in which characteristic X-rays generated from the specimen upon irradiation with an electron beam are detected, absorption current values of the specimen and a reference sample are measured before the final measurement, the value of ratio between thus measured values is determined, and the absorption current value of the specimen measured at the time of final measurement is multiplied by this value of ratio, so as to calculate the irradiation current value thereof, thereby substantially monitoring the irradiation current.

24 Claims, 7 Drawing Sheets

TO IRRADIATION CURRENT MEASURING SECTION

X-RAY ANALYZER HAVING AN ABSORPTION CURRENT CALCULATING SECTION

RELATED APPLICATIONS

This application claims the priority of Japanese Patent Application No. 11-080822 filed on Mar. 25, 1999, which is incorporated herein by reference.

BACKGROUND OF THE INVENTION

1. Field of the Invention

The present invention relates to an X-ray analyzer, mounted to a scanning electron microscope (SEM) or the like, for carrying out element analysis of a specimen according to characteristic X-rays emitted therefrom upon irradiation with electron beams; and an analyzing method using the same.

2. Description of the Prior Art

Among specimen observing apparatus such as scanning electron microscope (SEM) and the like, there have been known those which qualitatively or quantitatively analyze elements contained in a specimen by analyzing a spectrum of characteristic X-rays generated from the specimen upon irradiation with electron beams.

When elements contained in the specimen are to be analyzed quantitatively, it has been desired that, since the irradiation current value of electron beams with respect to the specimen fluctuates greatly, this value be monitored and the measured X-ray dose be calibrated based thereon in an energy dispersive X-ray analyzer, for example, so as to improve the accuracy in quantitative analysis.

However, it is not always easy to correctly measure the irradiation current value during the final analysis of the specimen. Therefore, in conventional techniques, it has been assumed, for example, that the irradiation current value of electron beams in SEM does not vary in a short period such as an analyzing time, and the irradiation current value is measured by use of a Faraday cage, or the irradiation current value is computed according to the measured X-ray dose of a specific reference sample, so as to determine the irradiation current value during the final analysis of the specimen.

However, the irradiation current value of electron beams in an SEM varies in a short period of time such as the final measuring time in practice, such that the assumed irradiation current value of electron beams differs from the actual one, thereby making it difficult to greatly improve the accuracy in quantitative analysis.

In view of such circumstances, it is an object of the present invention to provide an X-ray analyzer with a simple configuration which can determine an accurate irradiation current value of electron beams during measurement of a specimen when carrying out quantitative analysis of elements contained in the specimen by detecting characteristic X-rays generated from the specimen upon irradiation with the electron beams, thereby greatly improving the accuracy in analysis of elements contained in the specimen; and an analyzing method using the same.

In SEMs equipped with a field emission type (FEG type) electron gun, since the irradiation current of electron beams fluctuates more greatly than in other SEMs, it is necessary to monitor the irradiation current of electron beams during the final measurement of the specimen even if the configuration of the apparatus is somewhat complicated thereby.

Therefore, conventional FEG type SEMs use irradiation current measuring means or the like comprising a Faraday cage provided with an aperture for transmitting electron beams or the like, disposed on the electron beam source side from the specimen, so as to monitor a part of irradiation current of electron beams during the final measurement of the specimen, and calibrate the measured X-ray dose based thereon. In the FEG type SEMs, however, the cross-sectional intensity distribution of the irradiation current flux changes with time because of the fact that the surface state of the filament of the electron gun changes with time, and so forth, so that the irradiation current value detected by the irradiation current measuring means or the like is not proportional to the actual irradiation current value upon the specimen, whereby it has been difficult to greatly improve the accuracy in quantitative analysis.

In view of such circumstances, it is an object of the present invention to provide an X-ray analyzer which can determine a correct irradiation current value of electron beams during measurement of a specimen even when carrying out quantitative analysis of elements contained in the specimen by detecting characteristic X-rays generated from the specimen upon irradiation with the electron beams in an FEG type SEM, thereby greatly improving its accuracy in analysis; and an analyzing method using the same.

SUMMARY OF THE INVENTION

The present invention achieves the above-mentioned objects by monitoring an absorption current value which has a good proportional relationship with the irradiation current value of an electron beam irradiating the specimen, and determining the irradiation current value of the electron beam according to the result of monitoring.

Namely, a first X-ray analyzer in accordance with the present invention is an X-ray analyzer comprising an electron beam source for generating an electron beam, electron beam converging means for converging the electron beam onto a specimen, and an X-ray detecting section for detecting a characteristic X-ray generated from the specimen upon irradiation with the electron beam;

the X-ray analyzer comprising:
  an absorption current measuring section for measuring an absorption current value from the specimen and measuring an absorption current value from a reference sample disposed so as to be interchangeable with the specimen;
  a proportionality factor calculating section for calculating a value of ratio A between respective absorption current values in the specimen and reference sample; and
  reference sample absorption current calculating means for calculating, when the specimen is finally measured, an absorption current value of the reference sample at each measuring time by multiplying each measured absorption current value of the specimen by the value of ratio A determined by the proportionality factor calculating section.

A second X-ray analyzer in accordance with the present invention is an X-ray analyzer comprising an electron beam source for generating an electron beam, electron beam converging means for converging the electron beam onto a specimen, and an X-ray detecting section for detecting a characteristic X-ray generated from the specimen upon irradiation with the electron beam;

the X-ray analyzer comprising:
  an absorption current measuring section for measuring an absorption current value from the specimen;
  an irradiation current measuring section disposed at a part of positions where the electron beam passes;

a proportionality factor calculating section for calculating a value of ratio C between the absorption current value in the specimen measured by the absorption current measuring section and an irradiation current value measured by the irradiation current measuring section substantially simultaneously with when the absorption current value is measured by the absorption current measuring section; and means for calculating, when the specimen is finally measured, an irradiation current value to be measured by the irradiation current measuring section at each measuring time from an absorption current value in the specimen or a reference sample disposed interchangeable with the specimen by multiplying each measured absorption current value of the specimen by the value of ratio C determined by the proportionality factor calculating section.

A third X-ray analyzer in accordance with the present invention is an X-ray analyzer comprising an electron beam source for generating an electron beam, electron beam converging means for converging the electron beam onto a specimen, and an X-ray detecting section for detecting a characteristic X-ray generated from the specimen upon irradiation with the electron beam;

the X-ray analyzer comprising:

an absorption current measuring section for measuring an absorption current value from the specimen and measuring an absorption current value from a reference sample disposed so as to be interchangeable with the specimen;

an irradiation current measuring section disposed at a part of positions where the electron beam passes;

a current value ratio calculating section for calculating a value of ratio C between the absorption current value measured by the absorption current measuring section and an irradiation current value measured by the irradiation current measuring section substantially simultaneously with when the absorption current value is measured by the absorption current measuring section; and an apparatus comprising a storage section for storing a plurality of values of C, the apparatus comprising:

a current value ratio calculating and storing section for determining and storing respective ratio values Cstd, Csmp for the reference sample and specimen, a proportionality factor calculating section for determining a value of ratio K between the stored Cstd and Csmp, and reference sample absorption current calculating means for calculating, when the specimen is finally measured, an absorption current value of the reference sample at each measuring time by multiplying each measured absorption current value of the specimen by the value of ratio K determined by the proportionality factor calculating section.

A first analyzing method in accordance with the present invention is a method comprising the steps of irradiating a specimen with an electron beam generated from an electron beam source and converged onto the specimen, detecting a characteristic X-ray generated from the specimen upon irradiation with the electron beam, and analyzing an element contained in the specimen according to a result of the detection;

the method comprising the steps of:

before finally measuring the specimen, successively measuring an absorption current value from the specimen according to the electron beam irradiation and an absorption current value obtained from a reference sample disposed interchangeably with the specimen according to irradiation of the reference sample with the electron beam;

determining a value of ratio A between the absorption current value from the specimen and the absorption current value from the reference sample; and then when finally measuring the specimen, while measuring an absorption current value from the specimen according to the electron beam irradiation, multiplying thus measured absorption current value by the proportionality factor A, and using a result of the multiplication as a substitute for the irradiation current value for the specimen, thereby analyzing the element contained in the specimen.

A second analyzing method in accordance with the present invention is a method comprising the steps of irradiating a specimen with an electron beam generated from an electron beam source and converged onto the specimen, detecting a characteristic X-ray generated from the specimen upon irradiation with the electron beam, and analyzing an element contained in the specimen according to a en result of the detection;

the method comprising the steps of:

before finally measuring the specimen, measuring an absorption current value from the specimen according to the electron beam irradiation and, substantially simultaneously therewith, measuring an irradiation current value caused by the electron beam at a position where the electron beam passes;

determining a value of ratio C between thus measured values; and then when finally measuring the specimen, while measuring an absorption current value from the specimen according to the electron beam irradiation, multiplying thus measured absorption current value by the value of ratio C, and using a result of the multiplication as a substitute for the irradiation current value for the specimen, thereby analyzing the element contained in the specimen.

A third analyzing method in accordance with the present invention is a method comprising the steps of irradiating a specimen with an electron beam generated from an electron beam source and converged onto the specimen, detecting a characteristic X-ray generated from the specimen upon irradiation with the electron beam, and analyzing an element contained in the specimen according to a result of the detection;

the method comprising the steps of:

before finally measuring the specimen, measuring an absorption current value from a reference sample according to the electron beam irradiation and, substantially simultaneously therewith, measuring an irradiation current value caused by the electron beam at a position where the electron beam passes;

determining and storing a value of ratio Cstd between thus measured values;

measuring an absorption current value from the specimen according to the electron beam irradiation and, substantially simultaneously therewith, measuring an irradiation current value caused by the electron beam at a position where the electron beam passes;

determining and storing a value of ratio Csmp between thus measured values;

determining a value of ratio K, as a proportionality factor, between the value of ratio Cstd for the reference sample and the value of ratio Csmp for the specimen; and then when finally measuring the specimen, while measuring an absorption current value from the specimen according to the electron beam irradiation, multiplying thus measured absorption current value by the proportionality factor K, and using a result of the multiplication as a substitute for the irradiation current value for the specimen, thereby analyzing the element contained in the specimen.

In this specification, "absorption current" refers to, of the irradiation current of the electron beam irradiating the specimen and the like, the current absorbed in the specimen and the like without being released into the space.

In the X-ray analyzer and the analyzing method using the same in accordance with the present invention, as mentioned above, the absorption current value having a predetermined proportional relationship with the irradiation current value of the electron beam irradiating the specimen is measured before the final measurement, and the irradiation current value of the electron beam is monitored at the final measurement according to the result of measurement.

Thus constituted present invention is based on the following ideas:

Since the above-mentioned absorption current greatly varies due to the kind of specimen measured and the surface state thereof, it is hard to monitor a correct irradiation current value even when the absorption current Value is used as it is.

For example, in the case where specimens different from each other are irradiated with the same intensity of irradiation current, the respective absorption current values from these specimens may differ from each other in general.

As a consequence, letting Ia be the intensity of current value absorbed by a specimen upon irradiation with an irradiation current with an intensity Io, their proportionality factor Ac (=Io/Ia) varies for each specimen in general.

However, as long as the same specimen is measured, the absorption current value has a good proportional relationship with the irradiation current value when its surface state does not vary. Therefore, when the proportionality factor Ac for each specimen is calculated before the final measurement, and the measured absorption current value of the specimen at the final measurement is multiplied by the proportionality factor Ac, the irradiation current value that has conventionally been unavailable unless being measured with a Faraday cage or the like can be monitored over the whole period of the final measurement.

Namely, an absorption current value (Istd) in a reference sample is measured and, immediately thereafter, a specimen is set at a measuring position in place of the reference sample, so as to measure an absorption current value (Ismp). Thereafter, both of thus measured current values are used for determining a proportionality factor A (=Istd/Ismp). Subsequently, the absorption current value of the specimen is measured during the final measurement, and thus measured value is multiplied by A, whereby data identical to that measured when the absorption current of the reference sample is measured can be obtained.

Assuming that the relationship between the absorption current value of the reference sample and the irradiation current value of an electron beam therefor has been known beforehand, if the above-mentioned proportionality factor is determined before the final measurement of each specimen, the irradiation current value of the electron beam at the time of measurement can be calculated during the final measurement for any specimen once its absorption current value is measured.

Feeding back thus obtained irradiation current value data to the X-ray analyzer can improve the accuracy of quantitative analysis.

Instead of the above-mentioned proportionality factor A, the absorption current value of the specimen and the irradiation current value at that time may be measured before the final measurement, and the proportionality factor C may be determined by use of thus measured values, whereby effects similar to those mentioned above can be obtained.

DESCRIPTION OF THE PREFERRED EMBODIMENTS

In the following, embodiments of the present invention will be explained with reference to the accompanying drawings.

Figure 1:
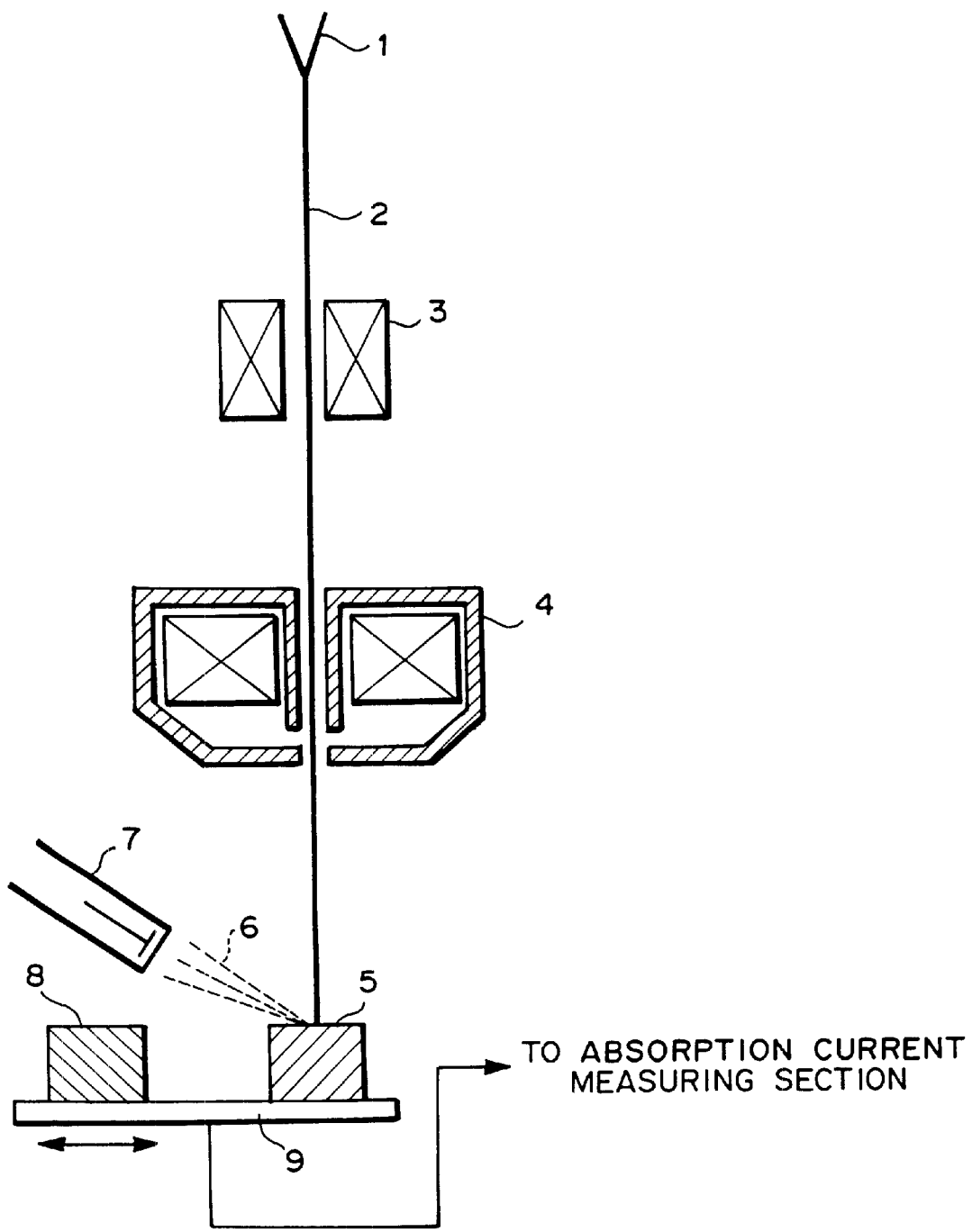
FIG. 1 is a schematic view showing a major part of the X-ray analyzer in accordance with an embodiment of the present invention.

FIG. 1 is a schematic view showing a major part of the X-ray analyzer in accordance with a first embodiment of the present invention mounted to a scanning electron microscope. In this X-ray analyzer, an electron beam 2 generated from a filament 1 of an electron gun, with its diameter being narrowed by a two-stage electromagnetic lens composed of a converging lens 3 and an objective lens 4, irradiates a specimen 5 to be analyzed.

The specimen 5 generates characteristic X-rays upon excitation with the electron beam. The characteristic X-rays 6 are detected by an energy dispersive X-ray analyzing section 7, so as to be used for qualitatively and quantitatively analyzing elements contained in the specimen 5.

While the intensity of specific X-ray spectrum of an element contained in the object to be analyzed is accurately measured so as to determine the content of this element in the quantitative analysis in such an X-ray analyzer, the intensity of the characteristic X-ray spectrum is proportional to the irradiation current value of the electron beam 2 irradiating the specimen 5.

Therefore, it is important that how the irradiation current value changes be monitored at least during the measuring period, so as to carry out calibration in the quantitative analysis of element based thereon.

Figure 7:
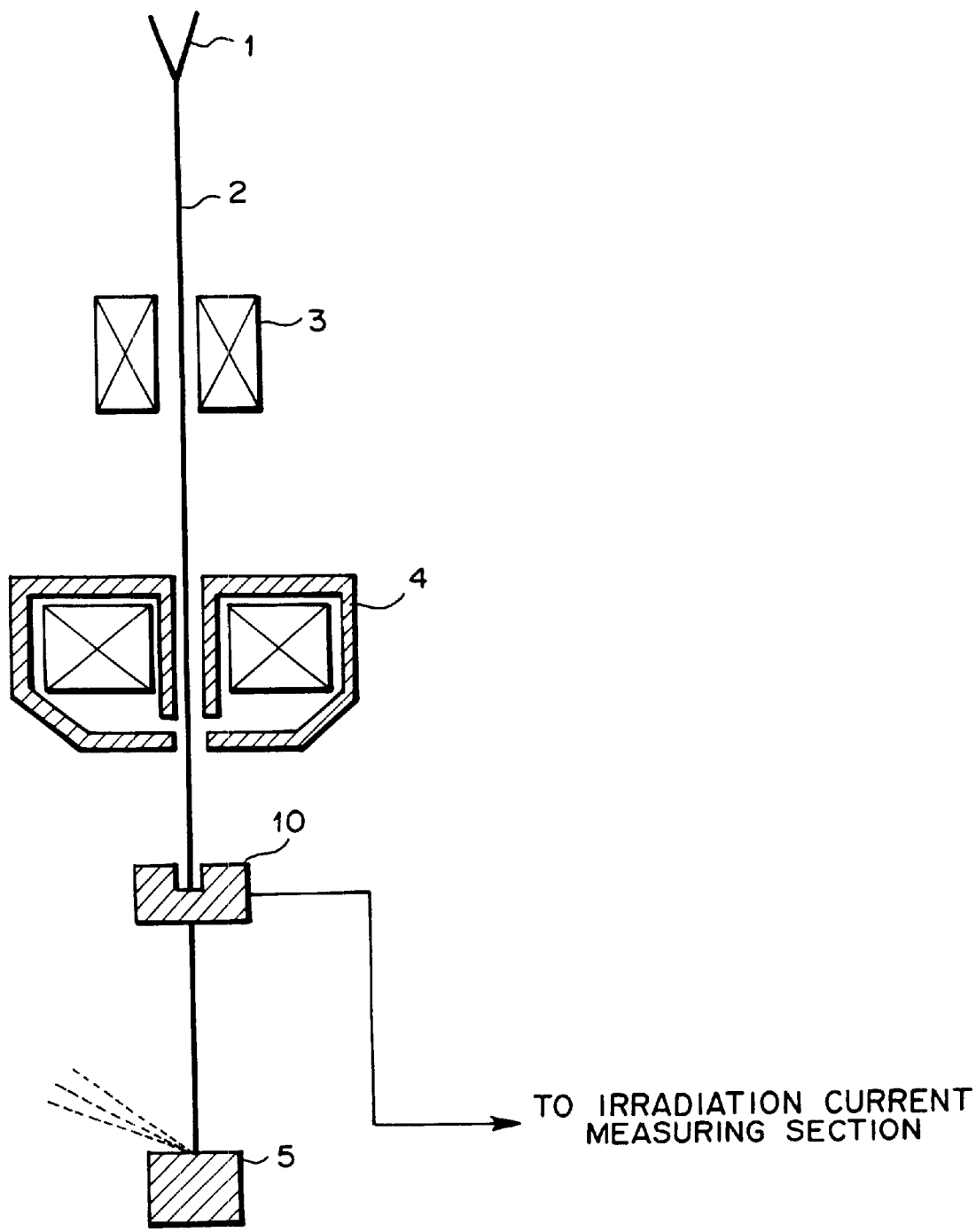
FIG. 7 is a schematic view showing a major part of a conventional X-ray analyzer.

For measuring the irradiation current value of the electron beam as such, it has been known to provide a Faraday cup (Faraday cage) 10 between the specimen 5 and the objective lens 4 as shown in FIG. 7, and detect the irradiation current by use of this Faraday cup (Faraday cage) 10 (specifically to detect the current cut by a movable stop of the converging lens 3, for example). According to this technique, however, the form of distribution of the beam cross section may vary due to changes in the surface state of the filament 1 even if the irradiation current value is constant, whereby the irradiation current may not be measured accurately over a long period of time.

Therefore, taking account of the fact that the absorption current value generated upon electron beam irradiation is proportional to the irradiation current value thereof, this embodiment measures absorption current values of the specimen 5 and a reference sample 8 before the final measurement, determines the value of ratio of thus measured values, and calculates the irradiation current value by multiplying the absorption current value of the specimen measured at the time of final measurement by the ratio value, thereby substantially monitoring the irradiation current.

Since the monitoring of the irradiation current is used for calibration when finally carrying out quantitative analysis based on characteristic X-rays, it will be sufficient if calculations are effected according to the absorption current measurement of the specimen 5 such that quantitative analysis upon irradiation with the same amount of irradiation current can be performed without actually calculating the irradiation current value.

Therefore, as shown in FIG. 1, this embodiment measures the absorption current value of each of the reference sample 8 and the specimen 5 before the final measurement of the specimen 5, calculates the value of ratio of thus measured values (proportionality factor), multiplies each measured value of the specimen 5 at the time of final measurement by thus calculated proportionality factor, and substantially determines the irradiation current value of the electron beam 2 according to thus obtained each absorption current value of the reference sample 8, thereby accurately effecting quantitative analysis of elements contained in the specimen. Here, the reference sample 8 is made of cobalt (Co) or the like in which the relationship between the spectral intensity of characteristic X-rays and the content of element is known. The reference sample 8 is mounted on a predetermined movable stage 9 together with the specimen 5. As this movable stage 9 is moved fast, absorption current values of the specimen 5 and reference sample 8 can be measured while the irradiation current value of the electron beam 2 does not change greatly.

A specific example of proportionality factor measurement will now be explained with reference to FIGS. 1 and 2.

First, the movable stage 9 is operated so as to set the reference sample 8 at a predetermined measuring position, the reference sample 8 is irradiated with the electron beam 2, and the absorption current value at this time is measured.

Figure 2:
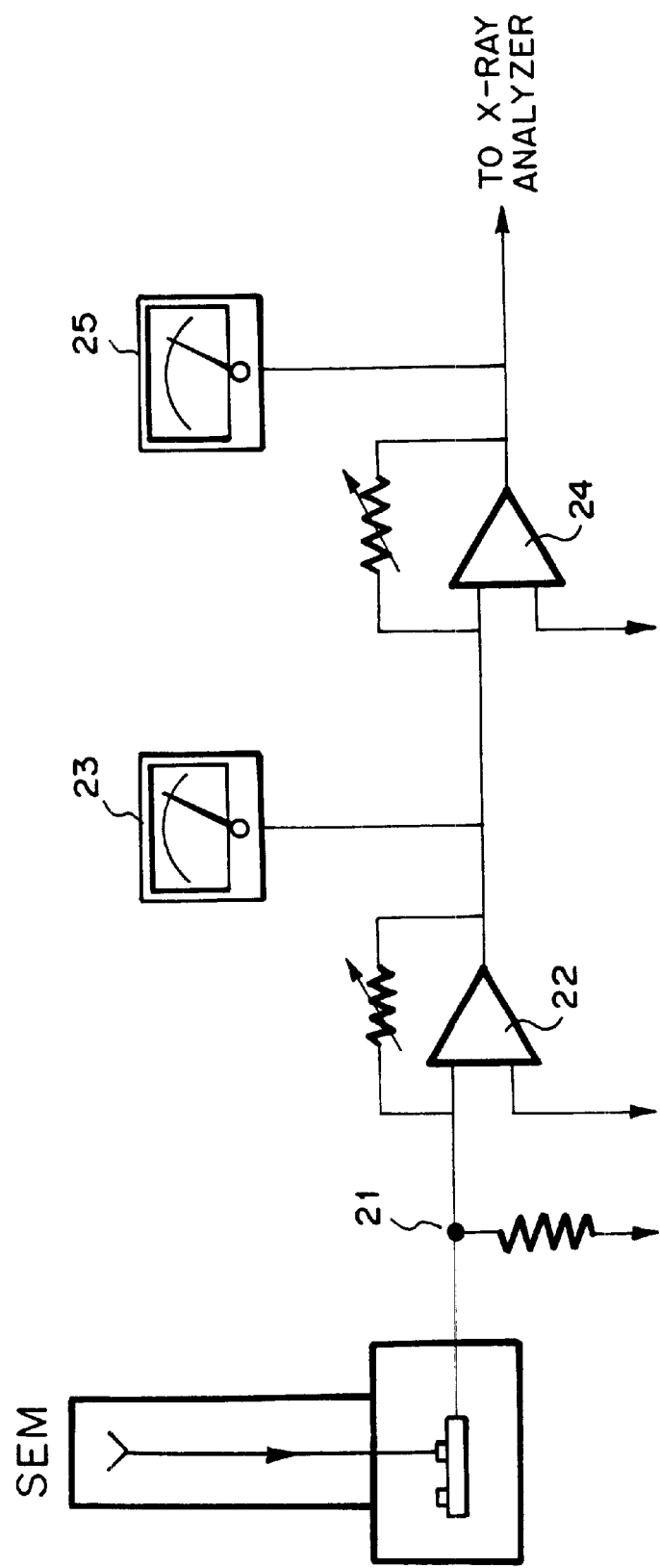
FIG. 2 is a schematic view showing an output value adjusting portion of the X-ray analyzer in accordance with the embodiment shown in FIG. 1.

Subsequently, as shown in FIG. 2, the absorption current from the reference sample 8 is measured in an absorption current measuring section. This absorption current measuring section comprises an absorption current detecting section 21, an input amplifier 22, an intermediate display section 23, an output amplifier 24, and an output display section 25. When the absorption current from the specimen 5 is to be measured, the gain of the input amplifier 22 is adjusted such that an appropriate voltage is displayed at the output display section 25, and this output voltage is recorded.

Immediately thereafter, the movable stage 9 is moved so as to set the specimen 5 at the measuring position, such that the electron beam 2 irradiates the specimen 5.

Then, the absorption current from the specimen 5 is measured in the absorption current measuring section. At this time, the gain of the output amplifier 24 is adjusted such that the measured absorption current value (output voltage value) of the reference sample 8 measured as mentioned above and the value displayed at the output display section 25 become identical to each other.

The gain adjustment effected here is an operation equivalent to setting a proportionality factor which is the ratio between the reference sample 8 and the specimen 5.

As a consequence, if the value of the output display section 25 is read out at the time of final measurement for the specimen 5, then a value substantially equivalent to that obtained when multiplied by the above-mentioned proportionality factor can be obtained for the absorption current value outputted from the specimen 5.

Thereafter, the absorption current value for the reference sample 8 multiplied by the proportionality factor is sent out to the X-ray analyzer, so that results similar to those obtained when the irradiation current value of the electron beam 2 is monitored can be obtained, whereby the quantitative analysis of elements contained in the specimen 5 can be carried out correctly.

Figure 3:
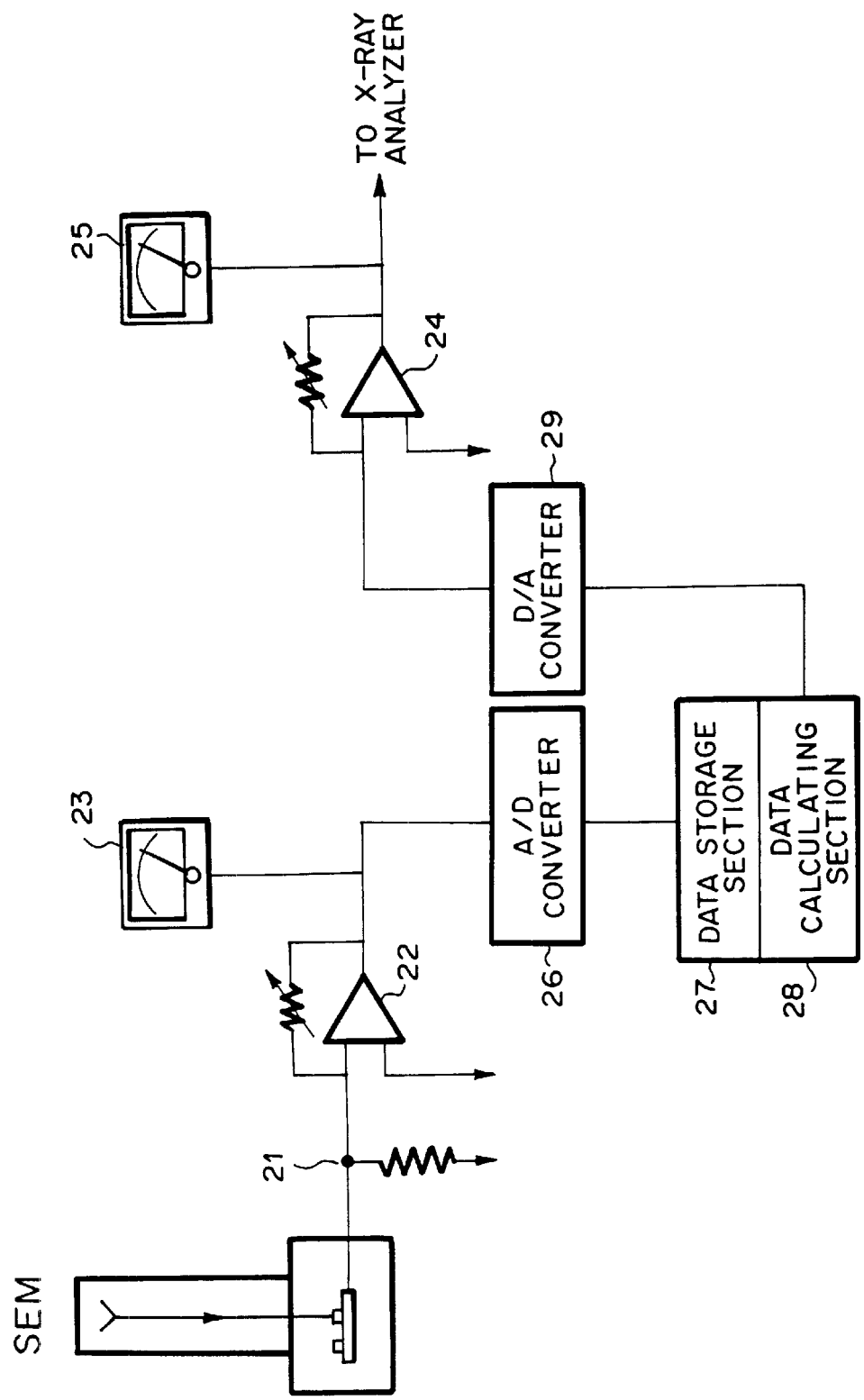
FIG. 3 is a schematic view showing a partly modified example of the output value adjusting portion shown in FIG. 2.

FIG. 3 is a block diagram showing a partly modified example of the one shown in FIG. 2. Namely, in this modified example, an A/D converter 26, a data storage section 27, a data calculating section 28, and a D/A converter 29 are disposed between the input amplifier 22 and the output amplifier 24.

This modified example is the same as the apparatus shown in FIG. 1 in that the reference sample 8 is moved to the measuring position, and the gain of the input amplifier 22 is regulated at the time when the absorption current value thereof is detected, so as to adjust the absorption current value to an appropriate voltage value. Here, however, the value outputted from the input amplifier 22 (the value (Istd) displayed at the intermediate display section 23) is A/D-converted at the A/D converter 26, and is stored in the data storage section 27 as a digital value.

Immediately thereafter, the movable stage 9 is moved so as to set the specimen 5 at a predetermined measuring position. While the gain of the input amplifier 22 is kept at the above-mentioned value, the value of absorption current (Ismp) from the specimen 5 outputted from the amplifier 22 is A/D-converted at the A/D converter 26, and is stored in the data storage section 27 as a digital value.

Then, the value or ratio (proportionality factor) A (=Istd/Ismp) between the respective absorption current values (Istd, Ismp) from the reference sample 8 and specimen 5 is calculated at the data calculating section 28, and the result of calculation is stored in the storage section 27.

Thereafter, every time a measured value of the final measurement is inputted to the data calculating section 28, the measured value is multiplied by the above-mentioned ratio value A stored in the data storage section 27, the result of this calculation is D/A-converted at the D/A converter 29, thus converted signal is amplified as an analog value by the output amplifier 24, so as to be sent out to the X-ray analyzer. Here, the gain of the output amplifier 24 is set to such a value that the sent-out signal value matches the sensitivity of the X-ray analyzer.

Figure 4:
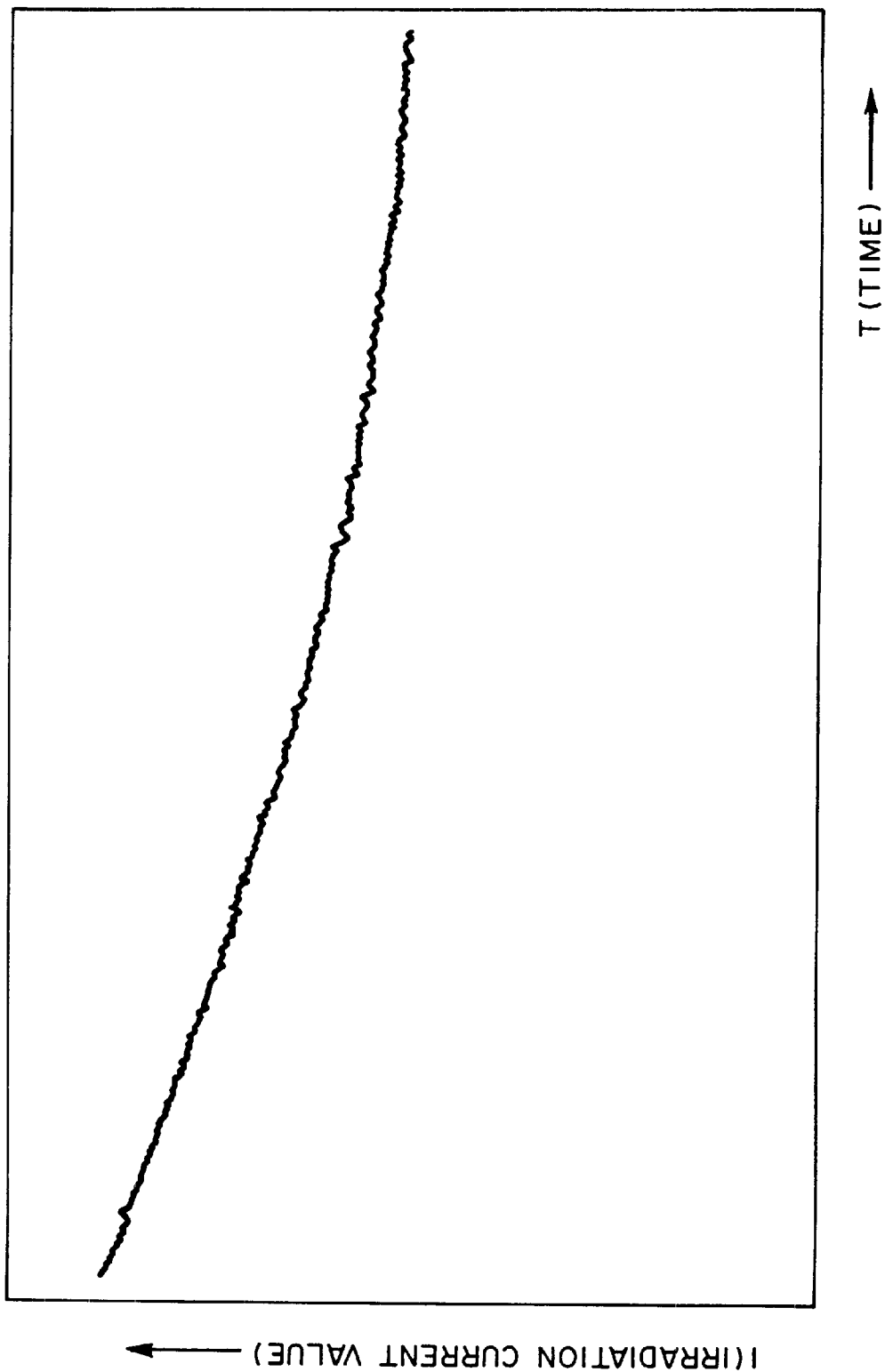
FIG. 4 is a graph showing changes in irradiation current.

Meanwhile, in the case of an FE-SEM (field emission type SEM) in particular, the irradiation current of the electron beam 2 gradually decreases as shown in FIG. 4. Therefore, even when the reference sample 8 and the specimen 5 are interchanged without loss of time as mentioned above, the irradiation current value may change therebetween. Hence, the above-mentioned proportionality factor A includes a slight fluctuation in absorption current accompanying the change in irradiation current value.

If the change in irradiation current value during the period when the reference sample 8 and the specimen 5 are interchanged is negligible, then the simpler technique in accordance with the above-mentioned embodiment is preferably used. If X-ray analysis with such a high accuracy that the above-mentioned change in irradiation current value is not negligible is to be carried out, then a technique in accordance with the following embodiment is preferably employed.

Figure 5:
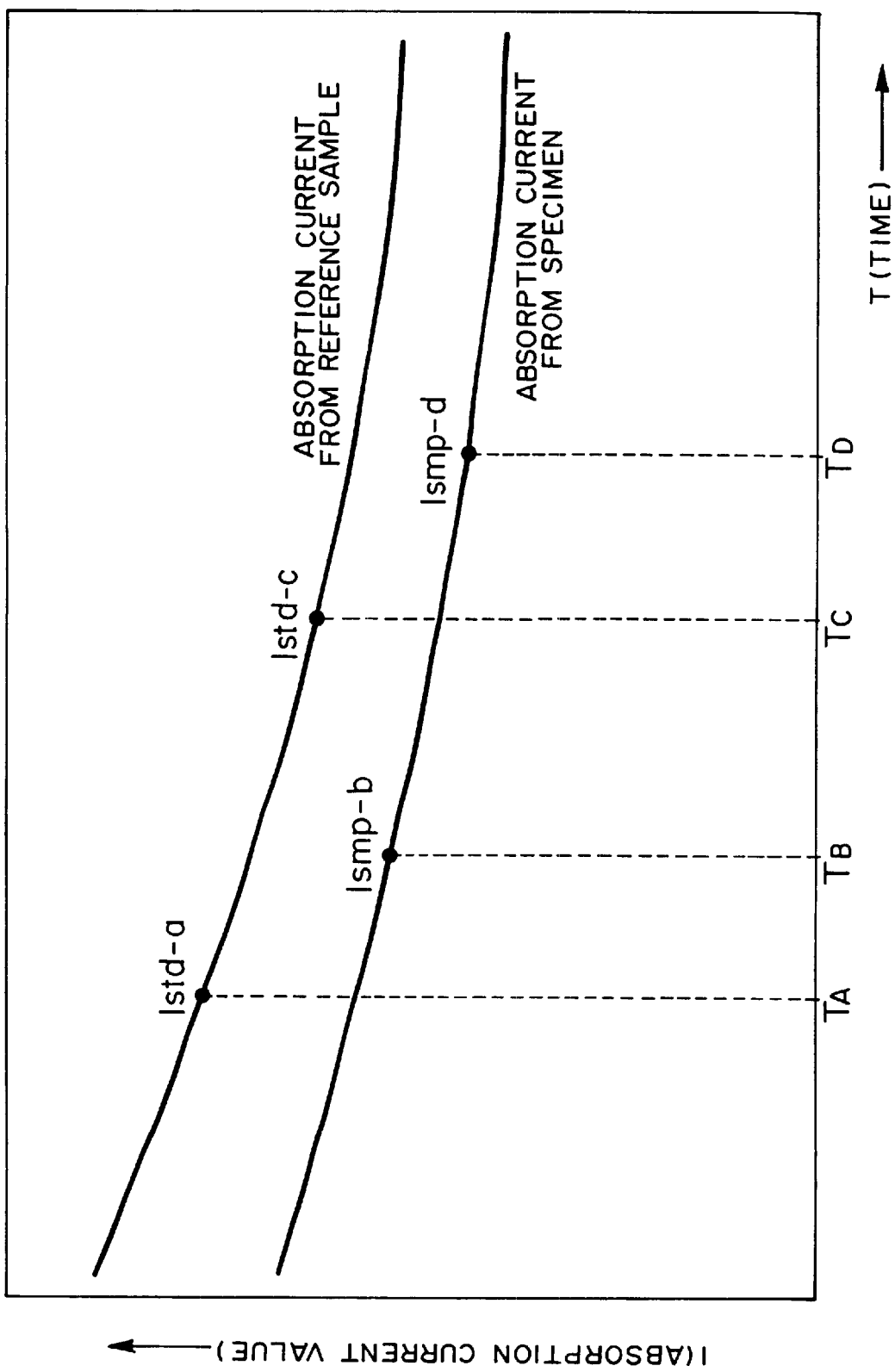
FIG. 5 is a graph for explaining an averaging process for determining a proportionality factor in the embodiment shown in FIG. 1.

In the case where the respective absorption current values of the reference sample 8 and specimen 5 change as shown in FIG. 5, the absorption current from the reference sample 8 and the absorption current from the specimen 5 are measured alternately.

For example, an absorption current value Istd_a from the reference sample 8 is measured at a point of time $T_A$, an absorption current value Ismp_b from the specimen 5 is measured at a point of time $T_B$, an absorption current value Istd_c from the reference sample 8 is measured at a point of time $T_C$, and then an absorption current value Ismp_d from the specimen 5 is measured at a point of time $T_D$. Thereafter, thus obtained absorption current values at four measuring points are operated, so as to determine a proportionality coefficient A with a higher accuracy than that mentioned above.

The reference sample 8 and the specimen 5 are quickly interchanged between the respective measuring steps in this case as well.

The absorption current values obtained at the respective measuring steps are successively stored in the data storage section 27.

Thereafter, the data of these four points are inputted to the following expression (1), so as to determine the proportionality factor A.

$$A=[(Istd\_a+Istd\ c)/\ (2\times Ismp\_b)+ 2\times Istd\_c/(Ismp\_b+Ismp\_d)]/2 \quad (1)$$

After the proportionality factor A is thus determined, the absorption current value from the specimen 5 measured at the time of final measurement is multiplied by this proportionality factor A, and thus multiplied value is outputted.

When the amounts of changes in the respective absorption current curves of the reference sample 8 and specimen 5 are thus determined, and the absorption current values at the subsequent points of time are estimated therefrom, then the measured absorption current values are averaged, whereby the accuracy in determining the proportionality factor can be improved.

Meanwhile, the irradiation current value of the electron beam 2 locally includes random noise while fluctuating so as to gradually decrease as shown in FIG. 4.

For eliminating influences of such random noise, it is desirable that, for example, a moving average process for averaging 16 measured values obtained at intervals of 0.1 second be carried out, and thus obtained average value be employed as the measured value at each measuring time mentioned above.

As a matter of course, the interval and number of the measuring points in the moving average process can be selected as appropriate.

In the above-mentioned embodiments, the value of ratio A between the respective absorption current values of the reference sample 8 and specimen 5 are determined, and the absorption current value from the specimen 5 at the time of final measurement is multiplied by this ratio value (proportionality factor) A, so as to calculate the absorption current value of the reference sample 8 at each measuring time. For the reference sample 8, the relationship between the irradiation current value of the electron beam and the absorption current value at that time has been known beforehand. Therefore, calculating the absorption current value of the reference sample 8 is equivalent to monitoring the irradiation current value of the electron beam 2 at that time.

However, it is possible to make a system which, without monitoring the irradiation current value of the electron beam via the absorption current value of the reference sample 8, determines the relationship between the irradiation current value of the electron beam 2 irradiating the specimen 5 and the absorption current value of the specimen 5 at that time as a proportionality factor C before the final measurement, and directly monitors and calculates the irradiation current value of the electron beam 2 at each measuring time by multiplying the absorption current value from the specimen 5 at the time of final measurement by this proportionality factor C.

In the case where the irradiation current value of the electron beam 2 is directly monitored as such, it is necessary for irradiation current detecting means to be disposed inside the electron beam in order to determine the proportionality factor C. It will be sufficient for the irradiation current detecting means in this case to be usable only when determining the proportionality factor C before the final measurement. Consequently, it is desirable that the irradiation current detecting means be configured so as to be freely inserted into and detracted from the electron beam.

In this embodiment, the irradiation current value data from the irradiation current detecting means can be measured during a very short period of time before the final measurement. Therefore, it is not influenced by changes in the intensity distribution in the cross section of the electron beam and the like, whereby there is no possibility of the accuracy finally lowering in the quantitative analysis of elements contained the specimen 5.

The above-mentioned embodiment is quite effective when the noise component in the irradiation current of the electron beam 2 is large. When the noise component is not so large, however, the following embodiment with a simpler method of determining a proportionality factor before the final measurement may be useful.

Figure 6:
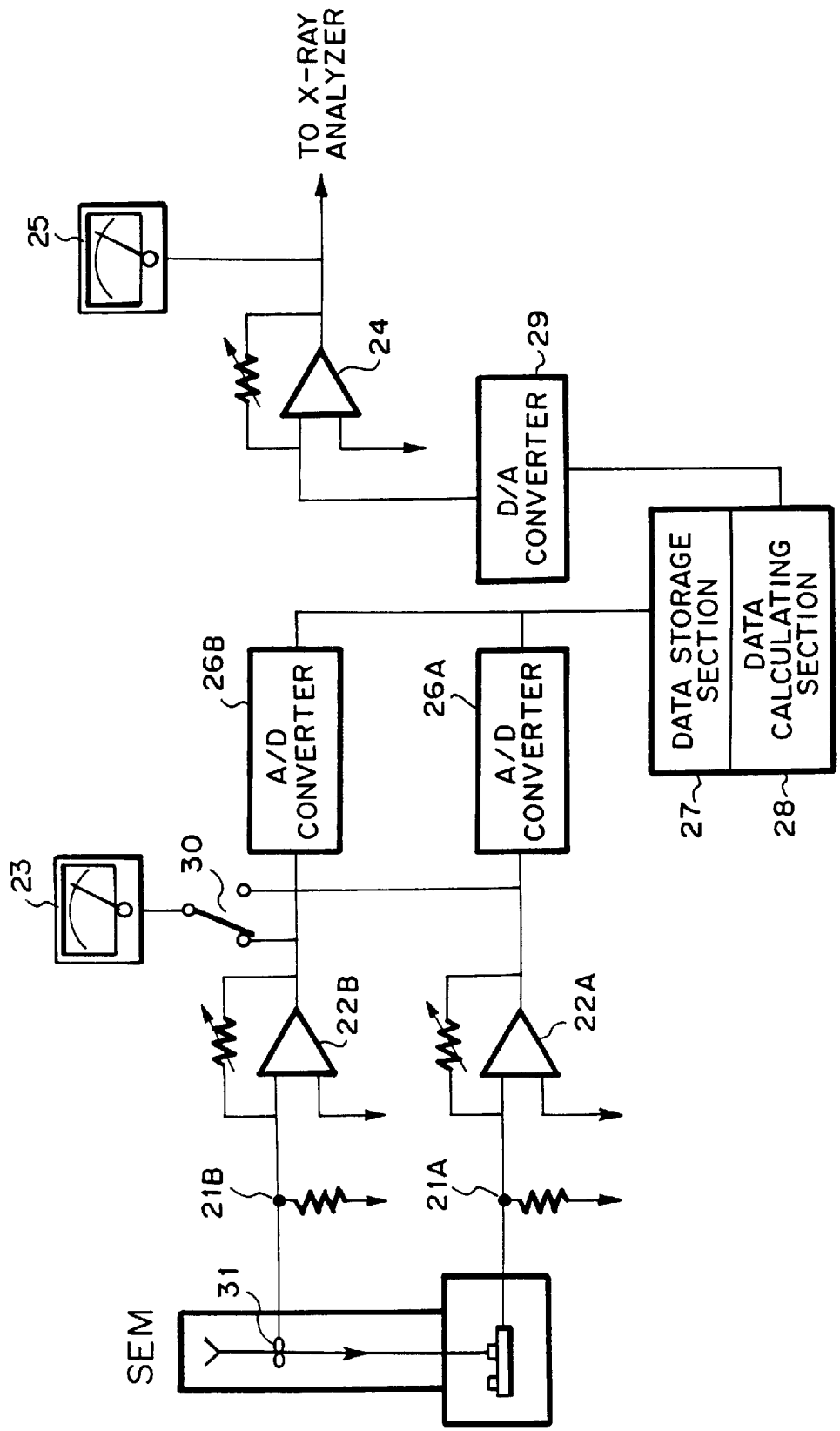
FIG. 6 is a schematic view showing an output value adjusting portion of the X-ray analyzer in accordance with an embodiment different from that shown in FIG. 1.

FIG. 6 is a schematic view showing an apparatus in accordance with this embodiment. The apparatus in accordance with this embodiment is equipped with an aperture type Faraday cage 31 for directly detecting the irradiation current of the electron beam 2; and further comprises an irradiation current measuring section for measuring this irradiation current value, and an absorption current measuring section for measuring absorption current values generated from the reference sample 8 and specimen 5 upon electron beam irradiation.

Namely, the absorption current values outputted from the reference sample 8 and specimen 5 are stored in a data storage section 27 by way of an absorption current detecting section 21A, an input amplifier 22A, and an A/D converter 26A. On the other hand, the irradiation current value detected at the Faraday cage 31 is stored in the data storage section 27 by way of an irradiation current detecting section 21B, an input amplifier 22B, and an A/D converter 26B.

Here, the data calculating section 28, D/A converter 29, output amplifier 24, and output display section 25 are configured similar to those in the above-mentioned embodiment. For monitoring the output values from the respective input amplifiers 22A, 22B, an intermediate display section 23 and a changeover switch 30 are provided.

The procedure of measurement using the apparatus of this embodiment will now be explained.

First, before the final measurement, the reference sample 8 is moved to the measuring position, the irradiation current of the electron beam 2 is detected by use of the aperture type Faraday cage 31 so as to measure an irradiation current value (Istd_i), and measure an absorption current value (Istd_a) of the reference sample 8 at the same time.

Since these measured values are stored in the data storage section 27 as mentioned above, the value of ratio Cstd (=Istd_a/Istd_i) between thus stored irradiation current value and absorption current value is determined at the data calculating section 28.

Subsequently, the specimen 5 is moved to the measuring position, an irradiation current value (Ismp_i) and absorption current value (Ismp_a) of the specimen 5 are measured in a manner similar to that mentioned above, and the value of ratio Csmp (=Ismp_a/Ismp_i) between thus measured irradiation current value and absorption current value is determined at the data calculating section 28.

After these two ratio values Cstd and Csmp are determined, a proportionality factor K corresponding to the proportionality factor C in the above-mentioned embodiment is determined according to the following expression (2):

$$K = Cstd/Csmp (= Istd/Ismp) \quad (2)$$

Since the irradiation current value and absorption current value have a very good proportional relationship therebetween within a very short period of time, the simultaneous measurement mentioned above can eliminate errors caused by fluctuations, thus making it possible to determine the proportionality factor K quite accurately.

Once the proportionality factor K is determined, the absorption current value from the specimen 5 can be multiplied by the proportionality factor K in the subsequent final measurement, whereby the irradiation current value during the final measurement can be monitored.

As a consequence, the irradiation current value can be seen accurately, whereby the absolute value accuracy of X-ray analysis can be improved greatly.

Without being restricted by the foregoing embodiments, the X-ray analyzer and analyzing method in accordance with the present invention can be modified in various manners. For example, the system mounting the X-ray analyzer is not restricted to the above-mentioned embodiments nor to SEMs.

While the movable stage mounting the reference sample and the specimen is provided in the above-mentioned embodiments, it may be of a type linearly movable along both X- and Y-axes or shaped like a turret adapted to rotate.

In the X-ray analyzer and the analyzing method using the same in accordance with the present invention, as explained in the foregoing, before the final measurement of a specimen, the absorption current of the specimen is measured, and only a simple calculation is carried out according to thus measured value, whereby the irradiation current value equivalent to that measured with a reference sample or with a Faraday cage can be monitored over a measuring period of the specimen. As a consequence, the accuracy in absolute quantitative analysis in the X-ray analyzer attached to a scanning electron microscope or the like can be improved easily and greatly.

What is claimed is:

1. An X-ray analyzer comprising an electron beam source for generating an electron beam, an electron beam converging section for converging said electron beam onto a specimen, and an X-ray detecting section for detecting a characteristic X-ray generated from said specimen upon irradiation with said electron beam;

said X-ray analyzer further comprising:
  an absorption current measuring section for measuring an absorption current value from said specimen and measuring an absorption current value from a reference sample disposed so as to be interchangeable with said specimen;
  a proportionality factor calculating section for calculating a value of ratio A between respective absorption current values in said specimen and reference sample; and
  a reference sample absorption current calculating section for calculating, when said specimen is finally measured, an absorption current value of said reference sample at each measuring time by multiplying each measured absorption current value of said specimen by the value of ratio A determined by said proportionality factor calculating section.

2. An X-ray analyzer according to claim 1, wherein said X-ray analyzer is a scanning electron microscope (SEM).

3. An X-ray analyzer according to claim 1, wherein said specimen and reference sample are mounted on a movable stage.

4. An X-ray analyzer according to claim 3, wherein said movable stage is linearly movable along X- and Y-axes.

5. An X-ray analyzer according to claim 3, wherein said movable stage rotates.

6. An X-ray analyzer according to claim 1, wherein said absorption current measuring section alternately measures absorption current values from said specimen and reference sample.

7. An X-ray analyzer according to claim 6, wherein said absorption current measuring section successively measures an absorption current value Istd_a from said reference sample at a point of time $T_A$, an absorption current value Ismp_b from said specimen at a point of time $T_B$, an absorption current value Istd_c from said reference sample at a point of time $T_C$, and an absorption current value Ismp_d from said specimen at a point of time $T_D$; and wherein said proportionality factor calculating section determines the value of ratio A according to the following expression:

$$A = [(Istd\_a + Istd\_c)/(2 \times Ismp\_b) + 2 \times Istd\_c/(Ismp\_b + Ismp\_d)]/2$$

8. An X-ray analyzer comprising an electron beam source for generating an electron beam, electron beam converging means for converging said electron beam onto a specimen, and an X-ray detecting section for detecting a characteristic X-ray generated from said specimen upon irradiation with said electron beam;

said X-ray analyzer comprising:
  an absorption current measuring section for measuring an absorption current value from said specimen and measuring an absorption current value from a reference sample disposed so as to be interchangeable with said specimen;
  a proportionality factor calculating section for calculating a value of ratio A between respective absorption current values in said specimen and reference sample; and
  reference sample absorption current calculating means for calculating, when said specimen is finally measured, an absorption current value of said reference sample at each measuring time by multiplying each measured absorption current value of said specimen by the value of ratio A determined by said proportionality factor calculating section.

9. An X-ray analyzer comprising an electron beam source for generating an electron beam, an electron beam converging section for converging said electron beam onto a specimen, and an X-ray detecting section for detecting a characteristic X-ray generated from said specimen upon irradiation with said electron beam;

said X-ray analyzer comprising:
an absorption current measuring section for measuring an absorption current value from said specimen;
an irradiation current measuring section disposed at a part of positions where said electron beam passes;
a proportionality factor calculating section for calculating a value of ratio C between the absorption current value in said specimen measured by said absorption current measuring section and an irradiation current value measured by said irradiation current measuring section substantially simultaneously when said absorption current is measured by the absorption current measuring section; and
a section for calculating, when said specimen is finally measured, an irradiation current value to be measured by said irradiation current measuring section at each measuring time from an absorption current value in said specimen or a reference sample disposed interchangeably with said specimen by multiplying each measured absorption current value of said specimen by said value of ratio C determined by said proportionality factor calculating section.

10. An X-ray analyzer according to claim 9, wherein said X-ray analyzer is a scanning electron microscope (SEM).

11. An X-ray analyzer according to claim 9, wherein said specimen and reference sample are mounted on a movable stage.

12. An X-ray analyzer according to claim 11, wherein said movable stage is linearly movable along X- and Y-axes.

13. An X-ray analyzer according to claim 11, wherein said movable stage rotates.

14. An X-ray analyzer according to claim 9, wherein said irradiation current measuring section is inserted into and detracted from said electron beam.

15. An X-ray analyzer comprising an electron beam source for generating an electron beam, electron beam converging means for converging said electron beam onto a specimen, and an X-ray detecting section for detecting a characteristic X-ray generated from said specimen upon irradiation with said electron beam;

said X-ray analyzer comprising:
an absorption current measuring section for measuring an absorption current value from said specimen;
an irradiation current measuring section disposed at a part of positions where said electron beam passes;
a proportionality factor calculating section for calculating a value of ratio C between the absorption current value in said specimen measured by said absorption current measuring section and an irradiation current value measured by said irradiation current measuring section substantially simultaneously when said absorption current is measured by the absorption current measuring section; and
means for calculating, when said specimen is finally measured, an irradiation current value to be measured by said irradiation current measuring section at each measuring time from an absorption current value in said specimen or a reference sample disposed interchangeably with said specimen by multiplying each measured absorption current value of said specimen by said value of ratio C determined by said proportionality factor calculating section.

16. An X-ray analyzer comprising an electron beam source for generating an electron beam, an electron beam converging section for converging said electron beam onto a specimen, and an X-ray detecting section for detecting a characteristic X-ray generated from said specimen upon irradiation with said electron beam;

said X-ray analyzer comprising:
an absorption current measuring section for measuring an absorption current value from said specimen and measuring an absorption current value from a reference sample disposed so as to be interchangeable with said specimen;
an irradiation current measuring section disposed at a part of positions where said electron beam passes;
a current value ratio calculating section for calculating a value of ratio C between the absorption current value measured by said absorption current measuring section and an irradiation current value measured by said irradiation current measuring section substantially simultaneously when said absorption current value is measured by said absorption current measuring section; and
an apparatus comprising a storage section for storing a plurality of values of C,
said apparatus comprising:
a current value ratio calculating and storing section for determining and storing respective ratio values Cstd, Csmp for said reference sample and specimen,
wherein $$Cstd = Istd\_a/Istd\_i$$

where Istd_a is an absorption current value of a reference sample and Istd_i is an irradiation current value of the reference sample, and $$Csmp = Ismp\_a/Ismp\_i$$

where Ismp_a is an absorption current value of a specimen and Ismp_i is an irradiation current value of the specimen,
a proportionality factor calculating section for determining a value of ratio K between said stored Cstd and Csmp, and
a reference sample absorption current calculating section for calculating, when said specimen is finally measured, an absorption current value of said reference sample at each measuring time by multiplying each measured absorption current value of said specimen by said value of ratio K determined by said proportionality factor calculating section.

17. An X-ray analyzer according to claim 16, wherein said X-ray analyzer is a scanning electron microscope (SEM).

18. An X-ray analyzer according to claim 16, wherein said specimen and reference sample are mounted on a movable stage.

19. An X-ray analyzer according to claim 18, wherein said movable stage is linearly movable along X- and Y-axes.

20. An X-ray analyzer according to claim 18, wherein said movable stage rotates.

21. An X-ray analyzer comprising an electron beam source for generating an electron beam, electron beam converging means for converging said electron beam onto a specimen, and an X-ray detecting section for detecting a characteristic X-ray generated from said specimen upon irradiation with said electron beam;

said X-ray analyzer comprising:
an absorption current measuring section for measuring an absorption current value from said specimen and measuring an absorption current value from a reference sample disposed so as to be interchangeable with said specimen;
an irradiation current measuring section disposed at a part of positions where said electron beam passes;
a current value ratio calculating section for calculating a value of ratio C between the absorption current value measured by said absorption current measuring section and an irradiation current value measured by said irradiation current measuring section substantially simultaneously when said absorption current value is measured by said absorption current measuring section; and
an apparatus comprising a storage section for storing a plurality of values of C,
said apparatus comprising:
a current value ratio calculating and storing section for determining and storing respective ratio values Cstd, Csmp for said reference sample and specimen,
wherein $$Cstd = Istd\_a/Istd\_i$$

where Istd_a is an absorption current value of a reference sample and Istd_i is an irradiation current value of the reference sample, and $$Csmp = Ismp\_a/Ismp\_i$$

where Ismp_a is an absorption current value of a specimen and Ismp_i is an irradiation current value of the specimen,
a proportionality factor calculating section for determining a value of ratio K between said stored Cstd and Csmp, and
reference sample absorption current calculating means for calculating, when said specimen is finally measured, an absorption current value of said reference sample at each measuring time by multiplying each measured absorption current value of said specimen by said value of ratio K determined by said proportionality factor calculating section.

22. An analyzing method comprising the steps of irradiating a specimen with an electron beam generated from an electron beam source and converged onto said specimen, detecting a characteristic X-ray generated from said specimen upon irradiation with said electron beam, and analyzing an element contained in said specimen according to a result of said detection;

said method comprising the steps of:
before finally measuring said specimen, successively measuring an absorption current value from said specimen according to the electron beam irradiation and an absorption current value obtained from a reference sample disposed interchangeably with said specimen according to irradiation of said reference sample with the electron beam;
determining a value of ratio A between the absorption current value from said specimen and the absorption current value from said reference sample; and then
when finally measuring said specimen, while measuring an absorption current value from said specimen according to the electron beam irradiation, multiplying thus measured absorption current value by said value of ratio A, and using a result of said multiplication as a substitute for the irradiation current value for said specimen, thereby analyzing said element contained in said specimen.

23. An analyzing method comprising the steps of irradiating a specimen with an electron beam generated from an electron beam source and converged onto said specimen, detecting a characteristic X-ray generated from said specimen upon irradiation with said electron beam, and analyzing an element contained in said specimen according to a result of said detection;

said method comprising the steps of:
before finally measuring said specimen, measuring an absorption current value from said specimen according to the electron beam irradiation and, substantially simultaneously therewith, measuring an irradiation current value caused by said electron beam at a position where said electron beam passes;
determining a value of ratio C between thus measured values; and then
when finally measuring said specimen, while measuring an absorption current value from said specimen according to the electron beam irradiation, multiplying thus measured absorption current value by said value of ratio C, and using a result of said multiplication as a substitute for the irradiation current value for said specimen, thereby analyzing said element contained in said specimen.

24. An analyzing method comprising the steps of irradiating a specimen with an electron beam generated from an electron beam source and converged onto said specimen, detecting a characteristic X-ray generated from said specimen upon irradiation with said electron beam, and analyzing an element contained in said specimen according to a result of said detection;

said method comprising the steps of:
before finally measuring said specimen, measuring an absorption current value from a reference sample according to the electron beam irradiation and, substantially simultaneously therewith, measuring an irradiation current value caused by said electron beam at a position where said electron beam passes;
determining and storing a value of ratio Cstd between thus measured values;
measuring an absorption current value from said specimen according to the electron beam irradiation and, substantially simultaneously therewith, measuring an irradiation current value caused by said electron beam at a position where said electron beam passes;
determining and storing a value of ratio Csmp between thus measured values;
wherein $$Cstd = Istd\_a/Istd\_i$$

where Istd_a is an absorption current value of a reference sample and Istd_i is an irradiation current value of the reference sample, and $$Csmp = Ismp\_a/Ismp\_i$$

where $Ismp\_a$ is an absorption current value of a specimen and $Ismp\_i$ is an irradiation current value of the specimen, determining a value of ratio K, as a proportionality factor, between said value of ratio Cstd for said reference sample and said value of ratio Csmp for said specimen; and then when finally measuring said specimen, while measuring an absorption current value from said specimen according to the electron beam irradiation, multiplying thus measured absorption current value by said proportionality factor K, and using a result of said multiplication as a substitute for the irradiation current value of said specimen, thereby analyzing said element contained in said specimen.

* * * * *